US007674488B2

(12) United States Patent
Masuda et al.

(10) Patent No.: US 7,674,488 B2
(45) Date of Patent: Mar. 9, 2010

(54) EXTERNAL COMPOSITION COMPRISING AN AQUEOUS EXTRACT OF RED VINE LEAVES AND AN ANTI-INFLAMMATORY AGENT

(75) Inventors: Kenji Masuda, Soka (JP); Kazuki Matsumoto, Sakura (JP); Minoru Okada, Inzai (JP); Koichi Takahashi, Tomisato (JP)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 228 days.

(21) Appl. No.: 11/061,556

(22) Filed: Feb. 18, 2005

(65) Prior Publication Data
US 2005/0271757 A1 Dec. 8, 2005

(30) Foreign Application Priority Data
Feb. 19, 2004 (EP) ................... 04003705

(51) Int. Cl.
*A61K 36/00* (2006.01)
(52) U.S. Cl. ...................... 424/774; 424/725
(58) Field of Classification Search .................. None
See application file for complete search history.

(56) References Cited

U.S. PATENT DOCUMENTS

| | | | | |
|---|---|---|---|---|
| 3,136,693 | A * | 6/1964 | Abeles ........................ | 424/766 |
| 4,339,435 | A | 7/1982 | Adachi et al. | |
| 4,897,270 | A | 1/1990 | Deutsch et al. | |
| 4,942,033 | A | 7/1990 | Aubert et al. | |
| 5,107,000 | A | 4/1992 | Lunder | |
| 5,629,339 | A * | 5/1997 | Wierzbicki et al. .......... | 514/456 |
| 5,780,060 | A | 7/1998 | Levy et al. | |
| 6,207,164 | B1 | 3/2001 | Kreuter et al. | |
| 6,210,680 | B1 * | 4/2001 | Jia et al. ..................... | 424/725 |
| 6,284,269 | B1 | 9/2001 | Struengmann et al. | |
| 6,297,218 | B1 | 10/2001 | Morazzone et al. | |
| 6,342,255 | B1 * | 1/2002 | De Gregorio ................ | 424/778 |
| 6,485,727 | B1 * | 11/2002 | Esperester et al. .......... | 424/774 |
| 6,579,543 | B1 * | 6/2003 | McClung .................... | 424/728 |
| 6,627,231 | B2 | 9/2003 | Soldati | |
| 6,689,161 | B2 | 2/2004 | Chen et al. | |
| 6,756,065 | B1 | 6/2004 | Merizzi | |
| 6,835,401 | B2 | 12/2004 | Soldati | |
| 6,991,816 | B2 | 1/2006 | Esperester | |
| 2002/0165270 | A1 | 11/2002 | Remacle | |
| 2002/0192834 | A1 | 12/2002 | Sand et al. | |
| 2003/0007988 | A1 | 1/2003 | Courtin | |
| 2003/0031739 | A1 | 2/2003 | Esperester | |
| 2003/0069528 | A1 | 4/2003 | Herz et al. | |
| 2004/0146539 | A1 * | 7/2004 | Gupta ........................ | 424/401 |
| 2004/0151769 | A1 | 8/2004 | Esperester et al. | |
| 2004/0151794 | A1 | 8/2004 | Sacher et al. | |
| 2004/0223962 | A1 * | 11/2004 | Riordan .................... | 424/94.63 |
| 2004/0234633 | A1 * | 11/2004 | Kim et al. .................. | 424/769 |
| 2005/0142235 | A1 | 6/2005 | Horie et al. | |
| 2005/0142236 | A1 | 6/2005 | Horie et al. | |
| 2005/0202110 | A1 | 9/2005 | Horie et al. | |
| 2005/0271757 | A1 | 12/2005 | Masuda et al. | |
| 2006/0068043 | A1 | 3/2006 | Esperester | |
| 2006/0198913 | A1 | 9/2006 | Sacher | |

FOREIGN PATENT DOCUMENTS

| | | | |
|---|---|---|---|
| CA | 2512149 | A1 | 7/2004 |
| EP | 0694305 | A1 | 1/1996 |
| FR | 2276959 | A1 | 6/1974 |
| GB | 934554 | | 8/1963 |
| JP | 59040853 | * | 3/1984 |
| RU | 2195262 | * | 12/2002 |
| WO | 9929331 | A1 | 6/1999 |
| WO | 0128363 | A1 | 4/2001 |
| WO | 02072118 | A1 | 9/2002 |
| WO | 2004-058227 | A1 | 7/2004 |

OTHER PUBLICATIONS

Kiesewetter et al. Arzneimittel-Forschung . 2000. vol. 50, No. 2, pp. 109-117.*
Bastin et al. Organic Process Res. Devel. 2000. vol. 4, pp. 427-435.*
Endotelon, Sanofi Pharma AG., Medecine et Hygiene (May 31, 1989) 47/1797 (1826).
Vigne Rouge (Red Vine-Vitis vinifer); monograph Ph. Franc. X (p. 1-4), Janvier, 1996.
Medicaments A Base De Plantes, pp. 55-60, 1996, Les Chiers De L'agence.
Tisserand, R. The Art of Aromatherapy, p. 14, 1997.
Council Directive 93/35/EEC of Jun. 14, 1993 amending for the sixth time Directive 76/768/EEC on the approximation of the laws of the Member States relating to cosmetic products; http://europa.eu.int/smartapi/cgi/sga_doc?smartapi!celexapi!prod!CELEXnumdoc&Ig=EN&numdoc=31993L0035&model=guichett Richtlinie 93/35/EWG of Jun. 14, 1993, Article 1, Paragraph 1 (English translation).

(Continued)

*Primary Examiner*—Christopher R. Tate
(74) *Attorney, Agent, or Firm*—Michael P. Morris; Mary-Ellen M. Devlin; David L. Kershner

(57) ABSTRACT

This invention relates to a new composition containing the effective concentration of an aqueous extract of red vine leaves (1) and an anti-inflammatory agent (2) for preventing or alleviating the discomfort associated with mild-to-moderate chronic venous insufficiency of the legs. The compositions according to this invention may also contain pharmaceutically or cosmically acceptable additives.

17 Claims, No Drawings

OTHER PUBLICATIONS

H. Hildebrandt (Publ.): "Psychyrembel-Klinisches Woerterbuch (258. Auflage)" 1998, Walter De Gruyter, Berlin XP002246308.
English Abstract; patent #EP 0366156; May 2, 1990, Ismail, R., Derwent patent abstract accession # 1990-133658.
Ministry of Social Affairs and Solidarity, "Medicines of Plant Origin", Official Bulletin No. 90/22bis, 1990, pp. 25, 26 and 37 (English translation).
French Pharmacopeia-IX Edition, 6th Supplement, Document of Records of Pharmaceutical Practice, Jul. 1980, Chapter IV (English translation).
Bezanger-Beauquesne, Pinkas et al, "Medicinal Plants from Temperate Zones" Second Edition, Paris, France 1990, p. 150 (English translation).
Pharmacopee Francaise X, 1996, List of current monographs Extract of vigne rouge, 1st paragraph, Extract of Red Vine (Dried) (English translation).
Red List 1998 Medicinal Register of the Pharmaceutical Industry, Germany, 1998, Nos. 83 048 and 83 084 Antistax® (English Translation).
Red List 2000, Medicinal Register for Germany (including the EU-Permits) Germany, Nos. 83 003.5 and 83 082 Antistax® (English Translation).
H. Beck, "The A to Z of Red Vine Leaves", PTA Heute No. 8. Aug. 1997, year 11, pp. 792-796 (English translation.
List & Hoerhammer, Hagers Handbook of Pharmaceutical Practice, 4th Edition, Germany, 1979, p. 500 (English Translation).
Pharmacopee Francaise X, 1996, List of current monographs, Red Vine (English translation).
Bruchhausen et al., Hagers Manual of Pharmaceutical Practice 5th Comprehensively revised edition, 1990, p. 132 (English translation).
P.H.List and P.C. Schmidt, "Medicines of Plant Origin", Institute of Pharmaceutical Technology at the University of Marburg, Scientific Publishing House, Stuttgart, Germany 1984 Translation of the German pp. 385 and 388 (Technologie pflanzlicher Arzneimittelzubereitungen, 1984, pp. 385 and 388).
R. Maffei Facino et al; „Free Radicals Scavenging Action and Antienzyme Activities of Procyanidines from Vitis vinifera,Anzneim-Forsch/Drug Res. 44(1), No. 5, 592-601.
Witzleb, E.; Munchener Medizinische Wochenschrift. 1979. vol. 121, No. 2, pp. 49-54, Medline Abstract.
Abu-Own et al.; J. Vascular Surg. 1994. vol. 20, No. 5, pp. 705-710.
Pasqualini et al., Phlebology, 1996. vol. 11, No. 3, pp. 117-120.
Ernst et al; Phlebology, 19889. vol. 4, No. 2, pp. 107-111.
Loew et al. Phlebology, 1998. vol. 13, No. 2, pp. 64-67.
K. Bauer et al, Pharmazeutische Technologie, 1993, 4th edition 1993, p. 302 (English Translation).
Cataldi et al., "Effectiveness of the Association of Alpha-Tocopherol, Rutin, Melilotus, and Centella Asiatica in the Treatment of Patients Affected by Chronic Venous Insufficiency". Minerva Cardioangiol. 2001. vol. 49, pp. 159-163.
Bhattaram et al., Pharmacokinetics and Bioavilability of Herbal Medicinal Products, Phytomedicine, 2002, Supplement III; pp. 1-33.
Consoli, A., "Chronic Venous Insufficiency: An Open Trial on Flebs Crema," Minerva Cardioangiologica, Aug. 2003, vol. 51, N. 4 pp. 411-416.
English Abstract, patent #EP0826372; Apr. 4, 1998; Emil Flachsmann AG; ThomsonPharma Abstract. See U.S. equivalent patent 6,207,164.
English Abstract; patent #FR2276059; Jun. 25, 1974, Institut National de la Recherche Agronomique; "Extraction of the Plant Pigments of the Vitamin P"; source Thomson Pharma.
English Abstract, patent publication # JP2001122791; May 8, 2001, Boehringer Ingelheim International GmbH; Meal Enhancer Comprising Aqueous Extract of Red Vine Leaf for Alleviation and prophylaxis of Chronic Venous Insufficiency in Lower Extremity; source patent abstracts of Japan.
Girre L. et al: "In Vitro Antiherpetic Activity of the leaves of the Red Vine Vitis-Vinifera" Fitoterapia., vol. 61, No. 3, 1990, pp. 201-206, XP000981757 IDB Holding, Milan., IT ISSN: 0367-326 p. 201-p. 202. -Biosis.
Constantini, A. et al: "Clinical and capillaroscopic evaluation of chronic uncomplicated venous insufficiency with procyanidins extracted from vitis vinifera" Database Medline 'Online US National Library of Medicine (NLM) Bethesda MD US, English abstract of: Constantini A; De Bernardi, T; Gotti A: "Valutazione clinica e capillaroscopica del trattamento dell'insuffizienza venosa cronica non complicate con oligomeri procianidolic, estratti da semi di vitis vinifera" Minerva Cardioangiologica, vol. 47, No. 1-2- 1999, pp. 39-26, Italy.
English Abstract; patent #EP0151987; Aug. 21, 1985; Ismail, R., Derwent patent abstract accession #1985-204614.
English Abstract; patent #DE 20209650; Feb. 5, 2007; Sterken B. Derwent patent abstract accession No. 2002-699721.
Kiesewetter, H., et al.: Efficacy of Orally Administered Extract of Red Vine Leaf As 195 (folia vitis viniferae) in Chronic Venous Insufficience (Stages I-II)-Arzneimittelforschumg-Drug-Research 50(1), No. 2 (2000) p. 109-117.
International Search Report for PCT/EP2005/001424 mailed Jun. 7, 2005.
Brambilla, L., et al; Efficacy and Tolerability of a Topical Product Containing Chlorhexidine Gluconate 0.1% and Allantoin 1% in the Treatment of Skin Lesions and Ulcers; Giornale Italiano di Dermatologia e Venereologia (1998) vol. 134, No. 4, pp. 391-394. (Abstract).
Galasso, U., et al; Use of Hyaluronic Acid in the Therapy of Varicose Ulcers of the Lower Limbs; Minerva Chirurgica (1978) vol. 33, No. 21, pp. 1581-1596.
Lohfink, H.-D.; Therapy of Chronic Venous Insufficiency - A Field of the Dermatologic Out-Patient Department; Zeitschrift Fuer Hautkrankheiten (1987) vol. 62, No. 2, pp. 125-135. (Abstract).
Raake, W., et al; Treatment of Superficial Thrombophlebitis; Hamostaseologie (2002) vol. 22, No. 4, pp. 149-153. (Abstract).
Udupa, A.L.; Anti-Inflammatory and Wound Healing Properties of Aloe Vera; Fitoterapia (1994) vol. 65, No. 2, pp. 141-145.

* cited by examiner

EXTERNAL COMPOSITION COMPRISING AN AQUEOUS EXTRACT OF RED VINE LEAVES AND AN ANTI-INFLAMMATORY AGENT

BACKGROUND OF THE INVENTION

1. Technical Field

The invention relates to compositions comprising an effective dose of an aqueous extract of red vine leaves and an anti-inflammatory agent for preventing or alleviating mild-to-moderate chronic venous insufficiency of the legs. The composition according to this invention also includes acceptable pharmaceutical or cosmetic additives. In addition, the compositions according to this inventions decrease or prevent subjective symptoms such as lassitude (listlessness), heavy legs, tired legs, sensation of tension, and pain associated with swelling of calves and ankles due to disorder of leg venous flow.

2. Brief Description of the Related Art

Presently, there are millions of people around the world who suffer from mild-to-moderate chronic venous insufficiency of the legs. This common condition is characterized by an inadequacy of the venous circulation to return blood from the legs to the heart. The lack of adequate venous return results in venous stasis and an increased pressure within the venous circulation, promoting the development of oedema and tissular water retention. Chronic venous insufficiency (CVI) is a functional disorder caused by persistent inadequacy of the venous return and is characterized clinically by edema, skin changes, and subjective complaints, such as tired, heavy legs, pain, or tingling sensations, which are typically amplified by standing upright and by high ambient temperatures. This dysfunction may be a source of major distress with a significant negative impact on the patient's overall well-being and quality of life.

Early stages (grade I) are characterized by coronal phlebectasia paraplantaris, subfascial congestion, and edema; grade II CVI is associated with low-grade skin changes, eczema, and lipodermatosclerosis. If untreated, grades I and II often progress to an advanced stage characterized by recurrent venous leg ulcers (grade III). The stress caused by the symptoms, even when relatively mild initially, and the risk of later complications call for appropriate supportive and preventive measures to be initiated in the early stages of CVI.

Although some patients, even at early stages, might require surgery (sclerotherapy and variceal surgery), the use of compression stockings with or without additional physiotherapy is the most common treatment approach. The effect of compression is merely mechanical, i.e., this approach does not affect or correct the related biological dysfunction (capillary fragility in particular). Furthermore, the treatment with compression stockings often lacks compliance because of cosmetic concerns and the overall inconvenience of the compressive stockings, in the summer in particular. Therefore there is an urgent need for alternative approaches that are effective, well-tolerated, and more convenient.

Extract of red vine leaves contains flavonol-glycosides, -glucuronides, and -flavonoids, with quercetin-3-O-beta-D-glucuronide and isoquercitrin (quercetin-3-O-beta-glucoside) as its main active ingredients. The range of their pharmacological actions has not yet been fully elucidated, but in-vitro studies indicate that they have antioxidant and anti-inflammatory properties and that they inhibit platelet aggregation and hyaluronidase and reduce edema, possibly by reducing capillary permeability. Preclinical in-vivo experiments demonstrated anti-inflammatory and capillary wall thickening effects.

Dietary supplements including an aqueous extract of red vine leaves are disclosed to prevent and reduce the discomfort relating to mild-to-moderate chronic venous insufficiency of the legs in WO 01/28363. However, there are no hints to compositions comprising an aqueous extract of red vine leaves and other active ingredients, such as anti-inflammatory agents given by WO 01/28363.

The German utility model DE 202 09 650 discloses a recipe of an aqueous balm for the care of legs of persons having venous discomfort comprising an extract of red vine leaves, Aloe Vera, extracts of Calendulae and horse chestnut, lavender oil, vitamins, and other ingredients. However, there is no hint to the prevention and reduction the discomfort relating to mild-to-moderate chronic venous insufficiency of the legs.

SUMMARY OF THE INVENTION

Surprisingly, potentiation of anti-inflammatory and anti-edematous action, index of pharmacological activities of an aqueous extract of red vine leaves, is found by combination of an anti-inflammatory agent with an aqueous extract of red vine leaves comparing the action itself. Moreover, composing mild anti-inflammatory agents resulted in safe compositions whose efficacy is potentiated for preventing and alleviating discomfort relating to mild-to-moderate chronic venous insufficiency of the legs with minimum or no adverse reactions.

The new compositions comprising an anti-inflammatory agent and an aqueous extract of red vine leaves potentiate the efficacy of prevention or relaxation for mild-to-moderate chronic venous insufficiency of the legs.

Therefore, this invention relates to new external compositions that comprise an effective dose of an aqueous extract of red vine leaves and an anti-inflammatory agent as pharmacological active substances and their efficacies are potentiated for preventing and relaxing mild-to-moderate chronic venous insufficiency of the legs.

A primary objective of this invention provides more effective external compositions for preventing and alleviating the discomfort associated with mild-to-moderate chronic venous insufficiency of the legs.

A further objective of this invention provides more effective external compositions including herb components and an anti-inflammatory agent. The herb components were manufactured pursuant to a controlled process that preserves the herbal effectiveness of the ingredients for preventing and/or alleviating the discomfort associated with mild-to-moderate chronic venous insufficiency of the legs.

Another objective of this invention provides more effective external compositions including herb components and an anti-inflammatory agent with minimum or no adverse event for safety of topical administration that prevent and/or alleviate the discomfort associated with mild-to-moderate chronic venous insufficiency of the legs.

The other objective of this invention provides more effective external pharmaceutical compositions and more effective external medicated cosmetic compositions for preventing and/or alleviating the discomfort associated with mild-to-moderate chronic venous insufficiency of the legs.

DETAILED DESCRIPTION OF THE INVENTION

This invention relates to external compositions for preventing or alleviating the discomfort associated with mild-tomoderate chronic venous insufficiency of the legs including an effective dose of an aqueous extract of red vine leaves and an anti-inflammatory agent.

The external composition of this invention consists of herbal ingredients derived from an aqueous extraction (*Extractum vitis viniferae e folium spissum et siccum*) of red vine leaves (*folia vitis viniferae*) and an anti-inflammatory agent.

The primary active ingredient of the external composition is the aqueous extract of red vine leaves (*foliae vitis viniferae* L.).

The term "aqueous extract of red vine leaves" in this invention means the aqueous or solid aqueous extract of red vine leaves manufactured pursuant to a controlled process that preserves the herbal effectiveness of the ingredients. The term "dried extract of red vine leaves" in this invention means dried, pure extract of the above aqueous extract of red vine leaves. The term "soft extract of red vine leaves" in this invention means soft extracts that is concentrated from 5 to 7 part of red vine leaves to one part. The term "liquid extract of red vine leaves" in this invention means liquid extracts that are prepared by resolving of soft extract of red vine leaves with solvent (60(V/V) % ethanol/water) by the ratio of 1:1.

Red vine leaves as starting material for the aqueous extract of red vine leaves in this invention is also known as "dyer," which are leaves of *vitis vinifera LINNE* with blackish-blue pericarp and a red pulp. Concentration of each polyphenol compound in red vine leaves and its composition are affected by various ecophysiological factors around. It is preferred that dried leaves of red vine containing at least 4% of total polyphenols and 0.2% of anthocyans are used as starting material in this invention. Red vine leaves characterized like those are harvested at a point of time where the content of flavonoids has reached an optimum, i.e., around the harvesting time of the grapes. Moreover, less than 15 cm length and less than 12 cm width of red vine leaves are preferable. The leaves are carefully dried and crushed. For extraction the leaves are cut to pieces of preferably 5 to 10 mm. To achieve a high content of flavonoids the extraction is done using purified water at elevated temperature, preferably at a temperature in the range of 60° C. to 80° C., over a time of at least 6 up to 10 hours. The preferred method is that of an exhaustive percolation.

The so-called fluid extract obtained in the process of the extraction may be directly used in the preparation of liquid dosage forms. In order to get a more concentrated extract, at least a part of the solvent is removed by use of a suitable evaporator preferably.

The thick extract is sterilized under heated-compressed condition, preferably at a temperature from 120° C. to 150° C. for 1 up to 30 seconds, more preferably at a temperature from 140° C. to 145° C. for 2 up to 5 seconds. The thick extract obtained in this step may again be directly used in the manufacturing of liquid dosage forms.

For the preparation of solid dosage forms, the thick extract is dried, for instance, by use of a vacuum drying oven or a vacuum drying conveyer. Carriers or excipients may be added during drying to facilitate further processing of the extract.

The aqueous extract of red vine leaves used in this invention by pure extract conversion of an aqueous extract of red vine leaves contains total flavonoids (quercetin-3-O-beta-D-glucuronide), preferably in the range of 0.625% to 25%, more preferably in the range of 1.25% to 12.5%, specially in the range of 2.5% to 10%.

In the case of topical application, to prevent and/or alleviate the discomfort of mild-to-moderate chronic venous insufficiency of the legs, the amount of the aqueous extract of red vine leaves in equivalent quantity of soft extract of red vine leaves is between 0.1 g and 20 g per 100 g (or 100 mL) of composition, preferably between 0.2 g and 10 g per 100 g (or 100 mL) of composition, more preferably between 0.3 g and 5 g per 100 g (or 100 mL) of composition, and further more preferably between 0.5 g and 3 g per 100 g (or 100 mL) of composition.

The amount of the aqueous extract of red vine leaves in equivalent quantity of liquid extract of red vine leaves is between 0.2 g and 40 g per 100 g (or 100 mL) of composition, preferably between 0.4 g and 20 g per 100 g (or 100 mL) of composition, more preferably between 0.6 g and 10 g per 100 g (or 100 mL) of composition, and further more preferably between 1 g and 6 g per 100 g (or 100 mL) of composition.

The compositions according to this invention include anti-inflammatory agents as second active ingredients in addition to above aqueous extract of red vine leaves, provided that Aloe Vera, extracts of horse chestnut and *Calendulae* spp., and/or lavender oil are excluded.

Anti-inflammatory agents used in this invention are not limited and determined if the agents contain anti-inflammatory action, however, for safety of this agent with minimum or no adverse event, anti-inflammatory agents with mild effects used in non-prescription drug, medicated cosmetics and cosmetics field for many years are preferable. In addition, types and dosage of anti-inflammatory agents change depending on whether this external composition is pharmaceutical products, medicated cosmetic product, or cosmetic product.

Examples of such anti-inflammatory agents are non-steroidal anti-inflammatory drugs (NSAIDs), heparinoid, capsaicin, zinc oxide, glycyrrhizic acid and its salts thereof, glycyrrhetic acid and its salts and derivatives thereof, allantoin and its derivatives thereof, hyaluronic acid and its salts thereof, azulene and its salts and derivatives thereof, crude drugs and herbs having the anti-inflammatory action, and etc. These anti-inflammatory agents can be used in one or mixed with more than two kinds.

Examples of such non-steroidal anti-inflammatory drugs are salicylic acid, methyl salicylate, glycol salicylate, ethylene glycol salicylate, indometacin, diclofenac, piroxicam, ketoprofen, felbinac, bufexamac, ufenamate, ibuprofen piconol, flurbiprofen, and etc.

Examples of such glycyrrhizic acid and its salts thereof are glycyrrhizic acid, dipotassium glycyrrhizinate, monopotassium glycyrrhizinate, trisodium glycyrrhizinate, monoammonium glycyrrhizinate, ammonium glycyrrhizinate, and etc.

Examples of such glycyrrhetic acid and its salts and derivatives thereof are glycyrrhetic acid, stearyl glycyrrhetinate, beta-glycyrrhetinic acid, carbenoxolone disodium (disodium succinoyl glycyrrhetinate), and etc.

Examples of such allantoin and its derivatives thereof are allantoin, aluminum chlorohydroxy allantoinate (alcloxa), and etc.

Examples of such hyaluronic acid and its salts thereof are hyaluronic acid, hyaluronate sodium, and etc.

Examples of such azulene and its salts and derivatives thereof are azulene, guaiazulene (1,4-dimethyl-7-isopropylazulene), azulene sulfonate sodium, sodium guaiazulene sulfonate, and etc.

Examples of such crude drugs and herbs having the anti-inflammatory action are turmeric (*Curcumae rhizome*), scutellaria root (*Scutellariae radix*), phellodendron bark (*Phellodendri cortex*), ginseng (*Ginseng radix*), coptis rhizome (*Coptidis rhizoma*), glycyrrhiza (*Glycyrrhizae radix*), cinnamon bark (*Cinnamomi cortex*), gentian (*Gentianae radix*), safflower (*Carthami Flos*), gardenia fruit (*Gardeniae fructus*), lithospermum root (*Lithospermi radix*), peony root (*Paeoniae radix*), ginger (*Zingiberis Rhizoma*), swertia herb (*Swertia japonica*), mulberry bark (*Mori cortex*), rhubarb (*Rhei rhizoma*), Japanese angelica root (*Angelicae radix*), capsicum (*Capsici fructus*), atractylodes rhizome (*Atractylodis rhizoma*), poria sclerotium (*Poria*), hydrangea (*Hydrangea serrata Seringe* var.), comfrey (*Symphytum officiale*), arnica (*Arnica montana*), ginko (*Ginko biloba*), St. John's wort (*Hypericum perforatum*), purple deadnettle (*Lamium purpureum L.*), olive (*Olea europaea*) leaves, German chamomile (*Chamomilla recutita*), fragrant wormwood (*Artemisia capillaris*), gardenia (*Gardenia jasminoides*), tall groundcover (*Sasa veitchii*), perilla (*Perilla frutescens* var. *crispa*), linden (*Tilia cordata Mill.*), white birch (*Betula platyphylla* var. *japonica*) bark, horsetail (*Equisetum arvense*), ground ivy (*Hedera helix*), sage (*Salvia officinalis*), mallow (*Malva sylvestris*), clove (*Pimenta syzygium*), calendula (*Calendula officinalis L.*), Houttuynia (*Houttuynia cordata Thunberg*), loquat (*Eriobotrya japonica Lindl.*) leaf, loofah (*Luffa cylindrica*), tree peony (*Paeonia suffruticosa*), pine (*Pinus sylvestris L.*) cone, house chestnut (*Aesculus hippocastanum L.*), mukurossi peel (*Spindus mukurossi*), peach (*Prunus persica*) leaf, cornflower (*centaurea cyanuns L.*), saxifrage (*Saxifraga stolonifera*), wormwood (*Artemisia princeps Pampan*), rosemary (*Rosemarinus officinalis L.*), chamomile (*Anthemis Nobilis*), burnet (*Sanguisorbae officinalis L.*), zanthoxvlum fruit (*Zanthoxyli fructus*), chamomile flower (*Chamomilla recutita flos*), camphor (*Cinnamomum camphora*)□devil's claw (*Harpagophytum procumbens*), fir needle oil (*Abies sibirica*)□ hay flower (*Graminis flos*), pine needle oil (*Pinus sylvestris*), stinging nettle (*Urtica dioica*), white willow bark (*Salix alba cortex*), witch hazel (*Hamamelis virginiana L.*), and etc. In addition, these crude drug and herb having anti-inflammatory action can be dried powder, extract, fluidextract, ctincture, oil, and etc.

Combination amount of anti-inflammatory agent used in this invention components changes depending on types of anti-inflammatory agents and categorization as pharmaceutical products or medicated cosmetic products, but the amount of anti-inflammatory agent is usually between 0.0001 g and 50 g per 100 g (or 100 mL) of composition.

Specifically, a combination amount of non-steroidal anti-inflammatory drugs is preferably between 0.01 g and 50 g per 100 g (or 100 mL) of composition, more preferably between 0.03 g and 20 g per 100 g (or 100 mL) of composition, and further more preferably between 0.05 g and 10 g per 100 g (or 100 mL) of composition.

A combination amount of heparinoid is preferably between 0.01 g and 1 g per 100 g (or 100 mL) of composition, more preferably between 0.02 g and 0.5 g per 100 g (or 100 mL) of composition, and further more preferably between 0.03 g and 0.3 g per 100 g (or 100 mL) of composition.

A combination amount of capsaicin is preferably between 0.0001 g and 1 g per 100 g (or 100 mL) of composition, more preferably between 0.0005 g and 0.5 g per 100 g (or 100 mL) of composition, and further more preferably between 0.001 g and 0.1 g per 100 g (or 100 mL) of composition.

A combination amount of zinc oxide is preferably between 0.001 g and 60 g per 100 g (or 100 mL) of composition, more preferably between 0.01 g and 20 g per 100 g (or 100 mL) of composition, and further more preferably between 0.1 g and 10 g per 100 g (or 100 mL) of composition.

A combination amount of glycyrrhizic acid and its salts thereof is preferably between 0.001 g and 2 g per 100 g (or 100 mL) of composition, more preferably between 0.005 g and 1.5 g per 100 g (or 100 mL) of composition, and further more preferably between 0.01 g and 1 g per 100 g (or 100 mL) of composition.

A combination amount of glycyrrhetic acid and its salts and derivatives thereof is preferably between 0.001 g and 3 g per 100 g (or 100 mL) of composition, more preferably between 0.005 g and 2.5 g per 100 g (or 100 mL) of composition, and further more preferably between 0.01 g and 2 g per 100 g (or 100 mL) of composition.

A combination amount of allantoin and its derivatives thereof is preferably between 0.001 g and 10 g per 100 g (or 100 mL) of composition, more preferably between 0.005 g and 5 g per 100 g (or 100 mL) of composition, and further more preferably between 0.05 g and 2 g per 100 g (or 100 mL) of composition.

A combination amount of hyaluronic acid and its salts thereof is preferably between 0.001 g and 10 g per 100 g (or 100 mL) of composition, more preferably between 0.005 g and 5 g per 100 g (or 100 mL) of composition, and further more preferably between 0.01 g and 2 g per 100 g (or 100 mL) of composition.

A combination amount of lactoferrin is preferably between 0.001 g and 5 g per 100 g (or 100 mL) of composition, more preferably between 0.005 g and 3 g per 100 g (or 100 mL) of composition, and further more preferably between 0.01 g and 1 g per 100 g (or 100 mL) of composition.

A combination amount of azulene and its salts and derivatives thereof is preferably between 0.001 g and 0.4 g per 100 g (or 100 mL) of composition, more preferably between 0.01 g and 0.3 g per 100 g (or 100 mL) of composition, and further more preferably between 0.02 g and 0.2 g per 100 g (or 100 mL) of composition.

A combination amount of crude drugs and herbs having the anti-inflammatory action is preferably between 0.001 g and 50 g per 100 g (or 100 mL) of composition, preferably between 0.01 g and 30 g per 100 g (or 100 mL) of composition, and more preferably between 0.02 g and 20 g per 100 g (or 100 mL) of composition.

Depending on dosage forms, the external composition of the present invention is applied directly onto the leg skin once or several times a day. And the composition may be massaged in thinly, starting from the foot and working up towards the thigh.

In addition to active ingredients mentioned above, the external compositions of the present invention may also include other active ingredients.

The external compositions described in the present invention can be used in any topical forms, such as creams, ointments, gel ointments, plasters, tapes, topical solutions, aerosols, lotions, tinctures, and the like. Any of these formulations may be prepared using regular methods. And any additives in common use may be used upon preparation of these formulations, if necessary.

These external dosage forms described in the present invention may be prepared using regular methods by adding generally available pharmaceutical additives and cosmetic additives, such as bases, excipients, binders, lubricants, superplasticizers, plasticizers, antifoaming agents, polish, foaming agents, antistatic agents, desiccant, moisturizing agents, surfactant, solubilizer, buffer agents, resolvents, solubilizing agents, solvents, diluents, stabilizers, emulsifying agents, suspension, suspending agents, dispersing agents, isotonizing agents, aerosol propellant, adsorbents, reducing agents, antioxidant, backing, wetting agents, wet modifier, filler, extender, adhesives, viscous agent, softeners, pH modifiers, antiseptics, preservatives, corrigent, refrigerative agents, flavoring agents, perfume, fragrance, coloring matters, and the like.

Examples of such additives are described in Japanese Pharmaceutical Excipients Directory 2000 (edited by Japan Pharmaceutical Excipients Council, issued by Yakuji Nippo, Ltd.), The Japan's Specifications and Standards for Food Additives (issued by Japan Food Additives Association), Japanese Standards of Quasi-drug Ingredients (edited by Society of Japanese Pharmacopoeia, issued by Yakuji Nippo, Ltd.), Japan Cosmetic Ingredients Dictionary 4$^{th}$ Edition (edited by Japan Cosmetic Industry Association, issued by Yakuji Nippo, Ltd.), The Comprehensive Licensing Standards Of Cosmetics by Category (edited by Society of Japanese Pharmacopoeia, issued by Yakuji Nippo, Ltd.), The Japanese Cosmetic Ingredients Codex (edited and issued by Yakuji Nippo, Ltd.), International Cosmetic Ingredient Dictionary, and Handbook Ninth Edition 2002 (edited by John A. Wenninger, issued by The Cosmetic Toiletry and Fragrance Association) and etc.

The compositions according to this invention can be provided as pharmaceutical products or medicated cosmic products. The compositions described in this invention are explained by the following practical examples. However, the scope of this invention is not limited to these practical examples.

EXAMPLE 1

Cream

The following ingredients were processed through a regular method to form cream at the total weight of 1 kg, added with sodium citrate to adjust at pH 5.5.

| Ingredient | Amount |
| --- | --- |
| Soft extract of red vine leaves | 28.2 g |
| Dipotassium glycyrrhizinate | 5.0 g |
| Salicylic acid | 4.0 g |
| White petrolatum | 50.0 g |
| Stearyl alcohol | 40.0 g |
| Glyceryl monostearate | 34.0 g |
| Polyoxyethylene (25) cetylether | 16.0 g |
| Medium chain fatty acid triglyceride | 120.0 g |
| Propylene glycol | 50.0 g |
| Citric acid | 0.1 g |
| Sodium citrate | Adequate amount |
| Antiseptics | Adequate amount |
| Purified water | Adequate amount |

EXAMPLE 2

Gel Ointment

The following ingredients were processed through a regular method to form gel ointments at the total weight of 1 kg, added with triethanolamine to adjust at pH 5.5.

| Ingredient | Amount |
| --- | --- |
| Liquid extract of red vine leaves | 12.5 g |
| Glycyrrhetic acid | 5.0 g |
| Salicylic acid | 4.0 g |
| Allantoin | 2.0 g |
| Isopropanol | 350.0 g |
| Propylene glycol | 50.0 g |
| Carboxyvinyl polymer | 20.0 g |
| Triethanolamine | Adequate amount |
| Purified water | Adequate amount |

EXAMPLE 3

Ointment

The following ingredients were processed through a regular method to form ointments at the total weight of 1 kg.

| Ingredient | Amount |
| --- | --- |
| Liquid extract of red vine leaves | 12.5 g |
| Methyl salicylate | 5.0 g |
| Glycyrrhizic acid | 1.0 g |
| Heparinoid | 1.0 g |
| Zinc oxide | 1.0 g |
| Sorbitan sesquioleate | 5.0 g |
| Light liquid paraffin | 50.0 g |
| White petrolatum | Adequate amount |

EXAMPLE 4

Plaster

The following ingredients were processed through a regular method to form adhesive masse at the total weight of 1 kg. The resulted adhesive masse was coated on the non-woven fabric to prepare the plasters.

| Ingredient | Amount |
| --- | --- |
| Soft extract of red vine leaves | 10.0 g |
| Glycol salicylate | 5.0 g |
| Arnica tincture | 5.0 g |
| House chestnut extract | 5.0 g |
| Japanese angelica root extract | 0.2 g |
| Glycyrrhizic acid | 0.2 g |
| Capsicum extract | 0.1 g |
| Hyaluronate sodium | 0.1 g |
| Polyoxyethylene (9) lauryl ether | 10.0 g |
| L-menthol | 5.0 g |
| Propylene glycol | 50.0 g |
| Concentrated glycerin | 150.0 g |
| D-sorbitol solution | 300.0 g |
| Sodium polyacrylate | 50.0 g |
| Carboxymethylcellulose sodium | 20.0 g |
| Eudragit E 100 | 0.5 g |
| Kaolin | 30.0 g |
| Sodium edetate | 0.5 g |
| Dried aluminum potassium sulfate | 5.0 g |
| Tartaric acid | 1.0 g |
| Antiseptics | Adequate amount |
| Purified water | Adequate amount |

We claim:

1. A composition, suitable for external administration, for the alleviation of mild-to-moderate chronic venous insufficiency (CVI) of the legs comprising: (i) an aqueous extract of red vine leaves, and (ii) a non-steroidal anti-inflammatory drug selected from the group consisting of indomethacin, diclofenac, piroxicam, ketoprofen, felbinac, bufexamac, ufenamate, ibuprofen piconol and flurbiprofen, wherein the drug is present in a form and in an amount adapted for the alleviation of mild-to-moderate chronic venous insufficiency (CVI) of the legs.

2. The composition according to claim 1, wherein the extract of red vine leaves is concentrated comprising from approximately 0.1 g to approximately 20 g of extract of red vine leaves per 100 g or 100 mL of total composition.

3. The composition according to claim 1, wherein the extract of red vine leaves is concentrated comprising from approximately 0.2 g to approximately 10 g of extract of red vine leaves per 100 g or 100 mL of total composition.

4. The composition according to claim 1, wherein the extract of red vine leaves is concentrated comprising from approximately 0.5 g to approximately 3 g of extract of red vine leaves per 100 g or 100 mL of total composition.

5. The composition according to claim 1, comprising from approximately 0.2 g to approximately 40 g of extract of red vine leaves per 100 g or 100 mL of total composition.

6. The composition according to claim 1, comprising from approximately 0.4 g to approximately 20 g of extract of red vine leaves per 100 g or 100 mL of total composition.

7. The composition according to claim 1, comprising from approximately 1.0 g to approximately 6.0 g of extract of red vine leaves per 100 g or 100 mL of total composition.

8. The composition according to claim 1, comprising from approximately 0.0001 g to approximately 50 g of the non-steroidal anti-inflammatory drug per 100 g or 100 mL of total composition.

9. The composition according to claim 1, wherein the weight ratio between the extract of red vine leaves and the non-steroidal anti-inflammatory drug is from approximately 1:500 to approximately 400,000:1.

10. A composition suitable for external administration, for the alleviation of mild-to-moderate chronic venous insufficiency (CVI) of the legs comprising: (i) a dried extract of red vine leaves, wherein the dried extract of red vine leaves is obtained by extraction from dried red vine leaves containing at least 4% of total polyphenols and at least 0.20% of anthocyans using purified water, and (ii) a non-steroidal anti-inflammatory drug selected from the group consisting of indomethacin, diclofenac, piroxicam, ketoprofen, felbinac, bufexamac, ufenamate, ibuprofen piconol and flurbiprofen, wherein the drug is present in a form and in an amount adapted for the alleviation of mild-to-moderate chronic venous insufficiency (CVI) of the legs.

11. The composition according to claim 10, wherein the extract of red vine leaves comprises from approximately 0.625% to approximately 25% by weight of flavonoids.

12. The composition according to claim 10, wherein the extract of red vine leaves comprises from approximately 2.5% to approximately 10% by weight of flavonoids.

13. A method for the alleviation of mild-to-moderate chronic venous insufficiency (CVI) of the legs comprising: administering to a subject in need thereof a composition comprising (i) an aqueous extract of red vine leaves, and (ii) a non-steroidal anti-inflammatory drug selected from the group consisting of indomethacin, diclofenac, piroxicam, ketoprofen, felbinac, bufexamac, ufenamate, ibuprofen piconol and flurbiprofen, wherein the drug is present in a form and in an amount adapted for the alleviation of mild-to-moderate chronic venous insufficiency (CVI) of the legs.

14. The method of claim 13, wherein the extract of red vine leaves is concentrated and the composition comprises from approximately 0.1 g to approximately 20 g of extract of red vine leaves per 100 g or 100 mL of total composition.

15. The method of claim 13, wherein the composition comprises from approximately 0.2 g to approximately 40 g of extract of red vine leaves per 100 g or 100 mL of total composition.

16. The method of claim 13, wherein the composition comprises from approximately 0.0001 g to approximately 50 g of the non-steroidal anti-inflammatory drug per 100 g or 100 mL of total composition.

17. A method for the alleviation of mild-to-moderate chronic venous insufficiency (CVI) of the legs comprising: administering to a subject in need thereof a composition comprising (i) a dried extract of red vine leaves, and (ii) a non-steroidal anti-inflammatory drug selected from the group consisting of indomethacin, diclofenac, piroxicam, ketoprofen, felbinac, bufexamac, ufenamate, ibuprofen piconol and flurbiprofen, wherein the drug is present in a form and in an amount adapted for the alleviation of mild-to-moderate chronic venous insufficiency (CVI) of the legs and the weight ratio between the dried extract of red vine leaves and the non-steroidal anti-inflammatory drug is from approximately 1:500 to approximately 400,000:1.

* * * * *